United States Patent [19]

Bryksa

[11] 4,317,239

[45] Mar. 2, 1982

[54] PROTECTIVE HELMET FOR THE RETARDED

[76] Inventor: Nicholas Bryksa, 293 Washington St., Phillipsburg, N.J. 08865

[21] Appl. No.: 146,230

[22] Filed: May 5, 1980

[51] Int. Cl.³ .............................................. A63B 71/10
[52] U.S. Cl. ........................................... 2/411; 2/424
[58] Field of Search .............................. 2/9, 411–416, 2/424

[56] References Cited

U.S. PATENT DOCUMENTS

| 600,778 | 3/1898 | Frazier | 2/413 |
| 3,555,561 | 1/1971 | Neis | 2/411 |
| 3,992,722 | 11/1976 | Rhee | 2/411 |
| 4,095,294 | 6/1978 | Winterbottom | 2/413 X |

Primary Examiner—Louis Rimrodt
Attorney, Agent, or Firm—Ruth Moyerman

[57] ABSTRACT

A protective helmet for persons with severe mental or motor disabilities is disclosed.

The helmet includes padded front, side, front chin and under chin pieces. Alternate embodiments include a reinforced face frame and, most importantly, a removable lightweight transparent face cover. The underchin area is also supplied with a reinforced edging or rim to fit securely against the wearer's neck to prevent the user from pulling the helmet from his head.

The face covering and the securing of the helmet around the head is preferably by lacing.

8 Claims, 10 Drawing Figures

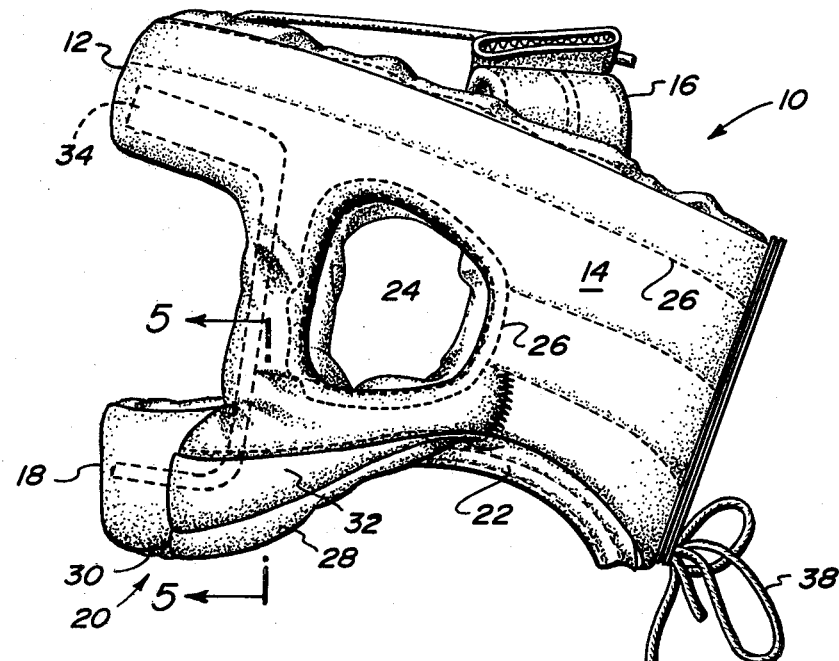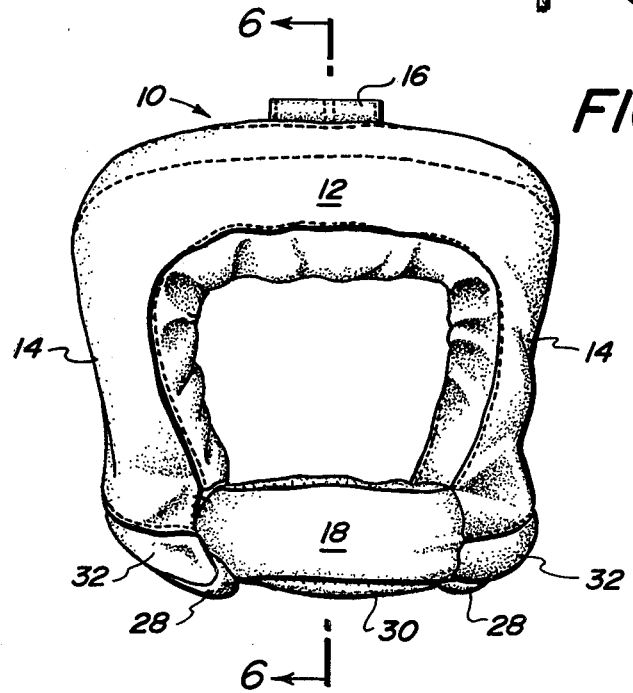

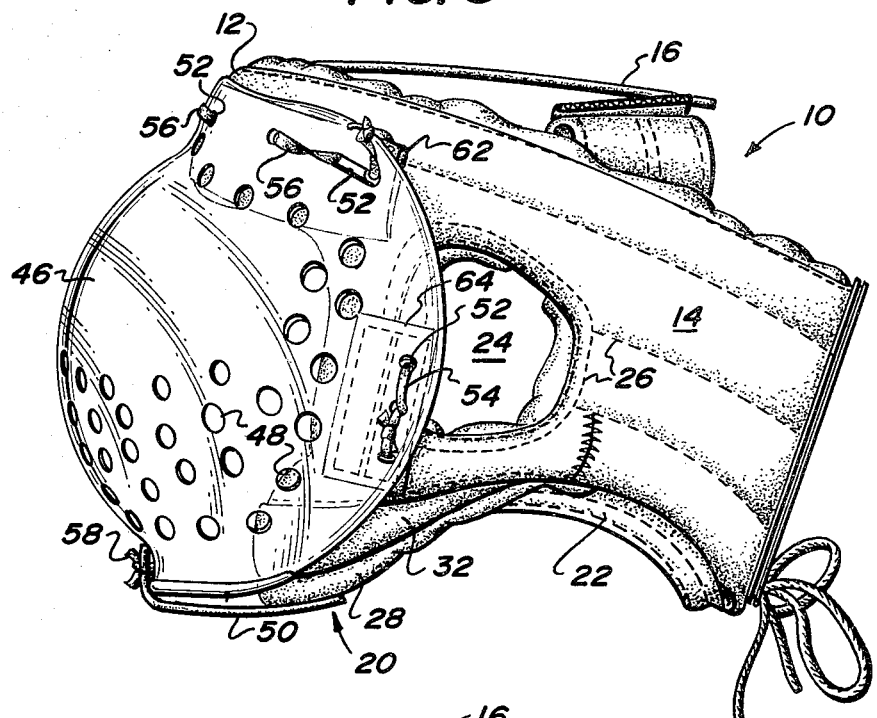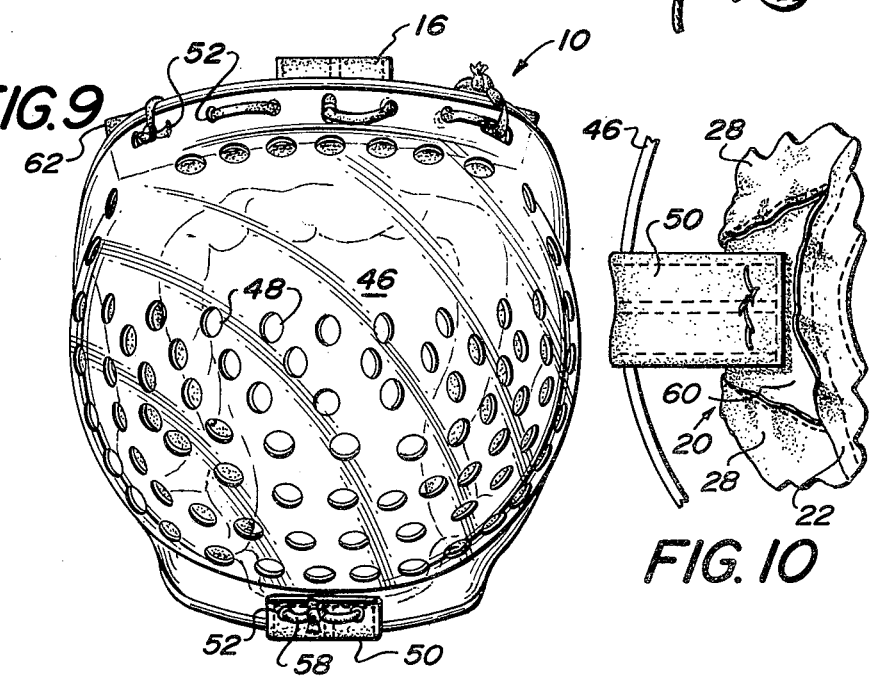

PROTECTIVE HELMET FOR THE RETARDED

BACKGROUND OF THE INVENTION

1. Field of the Invention

This invention relates to apparel and more particularly to protective headgear for the retarded.

2. Description of the Prior Art

The severely mentally retarded, or those persons with severe motor disabilities, are constantly in great danger of injury to the head. This injury may come about inadvertently because the person is incapable of controlling his movements and is thereby subject to falls and injuries from striking objects while falling. Additionally, among the severely retarded, it is not uncommon that the person inflicts injuries on himself by, for example, repeated striking of the head against hard objects or the poking of fingers or other sharp objects into the eyes. The under chin area and the eyes are, thus, particularly vulnerable to injury among this class of individuals.

In today's society the predominant, current theory is that all persons, if at all possible, should be in a conventional environment and should not be restricted in their movement.

Institutionalization is, therefore, in disfavor and committment to an institution is on the decline. Since many of these people are injured or cause injury to themselves if left unattended, there is now a greater need than ever for a type of protective headgear which will protect the wearer from injury while unattended. Furthermore the helmet, additionally must be constructed so that it is exceedingly difficult for the individual to remove the helmet himself.

While there are helmets on the market to protect boxers, wrestlers and other sports figures, this latter type of headgear is not suitable for the retarded for a variety of reasons, including the ease with which it can be removed by the individual, the lack of adequate padding and contouring under the chin and the general lack of faceguards designed for long periods of wear.

There is therefore a need for a protective helmet for the retarded which provides adequate chin protection.

There is also a need for a helmet which is not readily pulled off the head by the wearer.

There is finally a need for a suitable face cover which allows free breathing and ventilation but is suitable for long periods of wear.

SUMMARY OF THE INVENTION

The aforementioned prior art problems are solved by the protective helmet of this invention.

The helmet of this invention has padded side pieces and a padded forehead piece. The side pieces have an opening for the ears and the helmet is fastened preferably by lacing the side pieces at the back of the head. Where no face cover is employed, a front padded chin piece is also utilized. With or without a front face cover, the helmet includes an under chin padded area connected to the side pieces and to the front chin piece, if such is provided. The under chin padded area extends generally from ear to ear. In order to assure that the wearer cannot remove the helmet by pulling it from his head, the under chin piece includes a rim piece forming a continuous curved extension of the under chin piece and which causes the under chin piece to fit snuggly along the throat line of the wearer.

One alternate embodiment includes a reinforcing frame within the padded area of the helmet around the face to protect against excessive blows which might be received in that area.

Another, and most important, alternate embodiment includes a dome-shaped foraminous face cover designed to be removably attached to the helmet and which is intended to cover and protect the face of those individuals who are subject to self-inflicted injuries of the eyes. This face piece is foraminous to permit free breathing and the face piece is removable by preferably lacing it to the helmet.

It is therefore an object of this invention to provide a helmet suitable for persons with severe motor or mental disabilities to protect their heads, particularly the face and under chin area.

It is also an object of this invention to provide a protective face shield to prevent the wearer from biting himself or others and from putting foreign matter in the mouth.

It is a further object of this invention to provide a protective helmet which includes a transparent, lightweight, inexpensive and easily maintained face cover suitable for long periods of wear.

It is still another object of this invention to provide a helmet which is comfortable to the wearer and yet will protect him from severe face and head injuries.

It is yet another object of this invention to provide the foregoing helmet with a minimum of construction pieces to enable it to be easily and inexpensively assembled.

These and other objects may be more readily ascertainable to one skilled in the art from a consideration of the Figures and following description and exemplary embodiments.

BRIEF DESCRIPTION OF THE DRAWING(S)

FIG. 1 shows a side elevation of the helmet of this invention including a padded frontal chin piece and, showing in phantom, a rigid internal frame.

FIG. 2 shows a front elevation of the mask shown in FIG. 1.

FIG. 8 shows a side elevation including a face cover.

FIG. 9 shows a front elevation of the helmet of this invention including a face cover.

FIG. 10 shows a partial bottom elevation of the chin piece.

DESCRIPTION OF THE PREFERRED EMBODIMENT(S)

Figure 3:
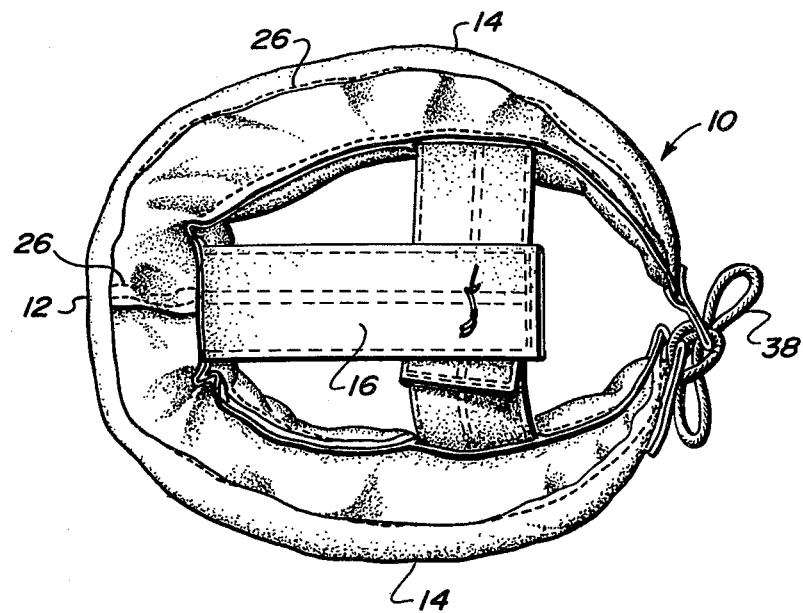
FIG. 3 shows a top elevation of the helmet of this invention.

Referring now to the drawings and more particularly to FIG. 1, helmet 10 is shown in side elevation including frontal piece 12, side piece 14, crown cover 16, frontal chin piece 18, chin underpiece 20 and under chin rim piece 22. Side piece 14 is shown including aperature 24 of a size and shape to allow an opening for the wearer's ear. Side piece 14 is also shown with stitching 26. In FIG. 1 and in other views it should be noted that chin underpiece 20 may be constructed of two or more panels including, in FIG. 1, panels 28, 30 and 32.

FIG. 1 also shows in phantom a side elevation of frame 34. Frame 34 is preferably constructed of steel or similar material, generally round in cross section and which encircles the entire wearer's face. The helmet need not necessarily include frame 34 but frame 34 is particularly suitable for circumstances in which it can be anticipated that the wearer might beat his head or otherwise subject that area of his body to severe blows.

The helmet illustrated in FIG. 1, and all the rest of the Figures, is padded and the top stitching shown at 26 provides reinforcing of the helmet.

Referring now to FIG. 2, a front elevation of the helmet shown in FIG. 1 is illustrated. In FIG. 2, the extent of the padding is more visible, together with the contoured fitting necessary to provide under chin piece 20.

FIG. 3 shows a top elevation of the helmet including a better view of crown cover 16. Crown cover 16 is shown as a T-strap connecting side pieces 14 and frontal piece 12. More top stitching 26 is also shown. In FIG. 3, and again with more particularity in FIG. 4, the means by which back pieces 14 are secured becomes visible.

Figure 4:
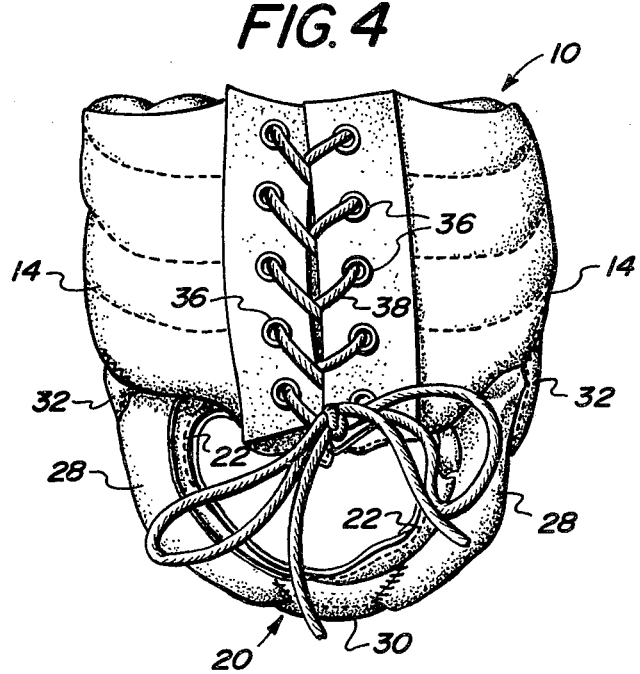
FIG. 4 shows a back elevation including eyelets and lacing.

Referring now to FIG. 4, it may be seen that side pieces 14 may be laced together through eyelets 36 with string 38.

Figure 5:
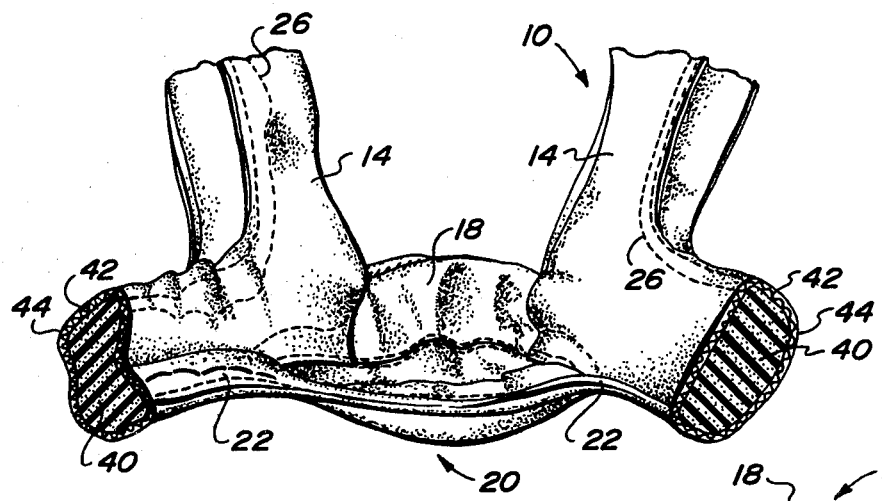
FIG. 5 shows a partial elevation taken on lines 5—5 of FIG. 1.

Referring now to FIG. 5, helmet 10 is shown in partial elevation as if the viewer were wearing the mask. In the view in FIG. 5, the very important underchin piece 20 is shown including its attachment to frontal chin piece 18 to give a continuous protective piece for the wearer. Also visible in FIG. 5 is the internal construction of the mask. Core padding 40 is shown surrounded by tear-resistant material 42 which is in turn surrounded by outer layer 44.

FIG. 5 is taken on lines 5—5 of FIG. 1.

Figure 6:
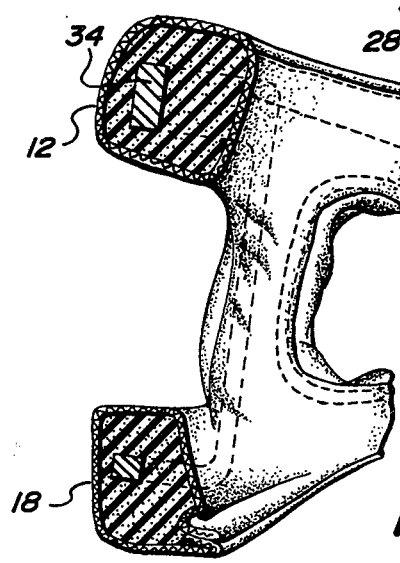
FIG. 6 shows a partial elevation taken on lines 6—6 of FIG. 2.

Referring now to FIG. 6, a view taken on lines 6—6 of FIG. 2, a partial cross section is shown of the mask including frame 34. Panel pieces 12, 14 and 18 are also shown.

Figure 7:
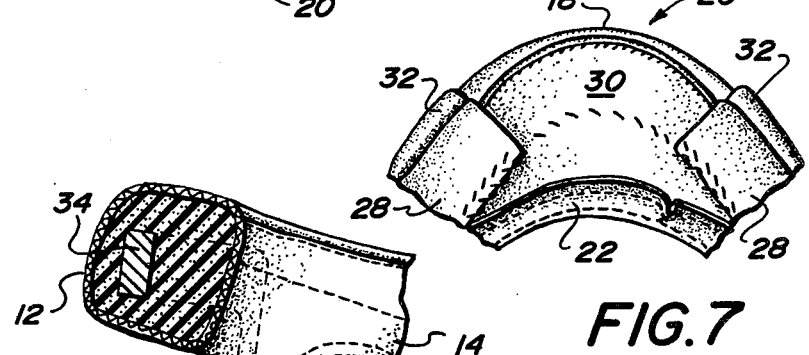
FIG. 7 shows a partial bottom elevation of the chin piece taken on lines 7—7 of FIG. 5.

Referring now to FIG. 7, a bottom elevation taken on lines 7—7 of FIG. 5 is shown. FIG. 7 illustrates the all-important chin under piece 20 including underchin rim piece 22. It may be noted that, in FIG. 7, underchin rim piece 22 is not necessarily padded and is preferably a folded down section of material, double stitched to resist stretching.

Referring now to FIG. 8, a very important alternate embodiment of this invention is illustrated. In FIG. 8, face cover 46 is added. Face cover 46 includes foramina 48 to enable the wearer to have adequate ventilation. When face cover 46 is included as a feature of the helmet, frontal chin piece 18 is omitted. FIG. 8 (and FIG. 9) show also reinforcing panel 62 and 64. Panel 62 is fastened to frontal piece 12 between frontal piece 12 and face cover 46. Reinforcing panel 64 is between side piece 14 and face cover 46. Strap 50 connects face cover 46 to panel 28 of chin underpiece 20. Face cover 46 may be laced to side piece 14 and frontal piece 12 by eyelets 52 and strings 54, 56 and 58.

Face cover 46 is preferably made of a clear, lightweight plastic and may be slightly flanged at its outer edge to facilitate fastening it to helmet 10.

Referring now to FIG. 9, a front elevation of face cover 46 is shown including a better view of the lacing of the face cover to the helmet.

Referring now to FIG. 10, a bottom elevation of the helmet of FIGS. 8 and 9 is shown. FIG. 10 illustrates a modification of chin underpiece 20 in which panel 60 is utilized to span the distance between panels 28. It is not necessary, in most applications, to pad panel 60 because the lower edge of face cover 46 gives sufficient protection in this area.

There are many variations which may be practiced within the scope of this invention.

The basic helmet, without chin guard or without the face shield but with extra padding, is useful for seizure patients and those with unsteady walking to protect the head when they fall. This helmet should include the under chin rim piece.

For the passive wearer, the helmet can be constructed without the second inner layer of tear resistant material. Also for the passive wearer, by utilizing straps 50 at the sides and chin underpiece, a half face shield may be used to prevent the wearer from putting his hand in his mouth.

Having now illustrated my invention it is not my intention that such illustrations be limiting to the invention, but that the invention be limited only by a reasonable interpretation of the apended claims.

What is claimed is:

1. A helmet to protect the head, including the face and chin, of persons with severe motor or mental disabilities comprising:
   (a) a padded frontal forehead piece of a height and width adapted to span the forehead of a wearer and terminating on each end in
   (b) two padded side pieces, said side pieces each being an identical, mirror image of the other, curved in construction to adapt to the contour of the wearer's head, extending on the wearer longitudinally from approximately cheekbone to approximately the center of the back of the wearer's head and vertically from the wearer's crown to chin bone and including an aperature placed so that the side piece surrounds but leaves open the ear;
   (c) a crown cover comprising a T-shaped strap connecting said frontal piece and each of said side pieces;
   (d) a padded frontal chin piece parallel to said forehead piece adapted to span the chin front of the wearer and terminating in said side pieces;
   (e) a generally arcuate, padded chin underpiece attached to and in alignment with said frontal chin piece and said side pieces so that said chin underpiece covers the entire under chin area of the wearer;
   (f) an under chin rim piece comprising a continuous, curved extension of said chin underpiece to cup said wearer's jowls to prevent the wearer from removing said helmet by pulling it from his head; and
   (g) means to removably secure said side pieces to each other at the back of the wearer's head whereby said wearer of said helmet is protected from injury on the sides, forehead, chin front and under chin area from contact injury.

2. The helmet according to claim 1 including, additionally, a reinforcing brace comprising a continuous rigid, internal frame structure within said helmet forehead piece, side pieces and frontal chin piece, surrounded by said helmet's padding to encircle the wearer's face to provide additional protection from savage blows.

3. The helmet according to claim 1 wherein said helmet material of construction includes a first outer layer of relatively smooth, durable material, and a second inner layer of tear resistant material surrounding a core of padding.

4. The helmet according to claim 1 wherein said chin underpiece comprises, on its external face, more than one fitted section.

5. A helmet to protect the head, including the face and chin, of persons with severe motor or mental disabilities comprising:
 (a) a padded frontal forehead piece of a height and width adapted to span the forehead of a wearer and terminating on each end in
 (b) two padded side pieces, said side pieces each being an identical mirror image of the other, curved in construction to adapt to the contour of the wearer's head, extending on the wearer longitudinally from approximately cheekbone to approximately the center of the back of the wearer's head and vertically from the wearer's crown to chin bone and including an aperature placed so that the side piece surrounds but leaves open the ear;
 (c) a crown cover comprising a T-shaped strap connecting said frontal piece and each of said side pieces;
 (d) a generally arcuate under chin piece attached to each of said side pieces;
 (e) an under chin rim piece comprising a continuous, curved extension of said chin underpiece to cup said wearer's jowls to prevent the wearer from removing said helmet by pulling it from his head;
 (f) a dome-shaped partially foraminous transparent face cover, said foramina being spaced to permit free breathing and ventilation;
 (g) means to removably attach said face cover to said helmet side and forehead pieces; and
 (h) means to removably secure said side pieces to each other at the back of the wearer's head whereby said wearer of said helmet is protected from injury on the sides, forehead, chin front and under chin area from contact injury.

6. The helmet according to claim 5 including, additionally,
 (i) chin strap means connecting said face cover to said chin underpiece.

7. The helmet according to claim 5 wherein the means of step (g) includes eyelets for lacing.

8. The helmet according to claims 1 or 5 wherein said means to secure helmet side pieces together includes eyelets for lacing.

* * * * *